US00PP30275P3

(12) United States Plant Patent
Suphachadiwong

(10) Patent No.: US PP30,275 P3
(45) Date of Patent: Mar. 5, 2019

(54) ***VANDA* PLANT NAMED 'SPCDW1516'**

(50) Latin Name: ***Vanda* Jones ex R. Br.**
Varietal Denomination: SPCDW1516

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 80 days.

(21) Appl. No.: 15/530,046

(22) Filed: Nov. 23, 2016

(65) Prior Publication Data

US 2017/0156251 P1 Jun. 1, 2017

(30) Foreign Application Priority Data

Nov. 27, 2015 (QZ) ..... PBR 2015/2863

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Keith O. Robinson
(74) *Attorney, Agent, or Firm* — Samuel R. McCoy, Jr.

(57) ABSTRACT

A new and distinct *Vanda* cultivar named 'SPCDW1516' which is characterized by a large quantity of flower with nearly white sepals and petals which are lightly suffused with yellow-green, a labellum with nearly white lateral lobes which are dotted purple and yellow at the base and a yellow-green central lobe, as well as the stability of these characteristics from generation to generation.

4 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1516'.

CROSS REFERENCE TO RELATED APPLICATIONS

This application claims priority to the Community Plant Variety Rights application number 2015/2863, filed Nov. 27, 2015, which is herein incorporated by reference.

BACKGROUND OF THE INVENTION

Parentage: The *Vanda* variety 'SPCDW1516' originated as a naturally occurring, whole-plant mutation of *Vanda* 'SPCDW1001' (unpatented in the United States, Community Plant Variety Rights grant number 29778), a variety developed and owned by the inventor. The inventor of 'SPCDW1516' is a commercial producer of *Vanda* and regularly discovers mutations at his greenhouse operation in Bangphra, Thailand. The variety now called 'SPCDW1516' was initially discovered in November of 2009 as one such mutation of 'SPCDW1001'.

Asexual Reproduction: Asexual reproduction of the new cultivar 'SPCDW1516', by way of mericloning, was first initiated in September of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1516' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1516'. These characteristics in combination distinguish 'SPCDW1516' as a new and distinct *Vanda* cultivar:

1. *Vanda* 'SPCDW1516' exhibits a large quantity of flowers; and
2. *Vanda* 'SPCDW1516' exhibits white flower petals when fully opened; and
3. *Vanda* 'SPCDW1516' exhibits a white dorsal sepal when fully opened; and
4. *Vanda* 'SPCDW1516' exhibits lateral sepals which are white and lightly suffused with yellow-green when fully opened; and
5. *Vanda* 'SPCDW1516' exhibits a labellum with nearly white lateral lobes which are dotted purple and yellow at the base and a yellow-green central lobe.

BOTANICAL DESCRIPTION OF THE PLANT

Figure 1:
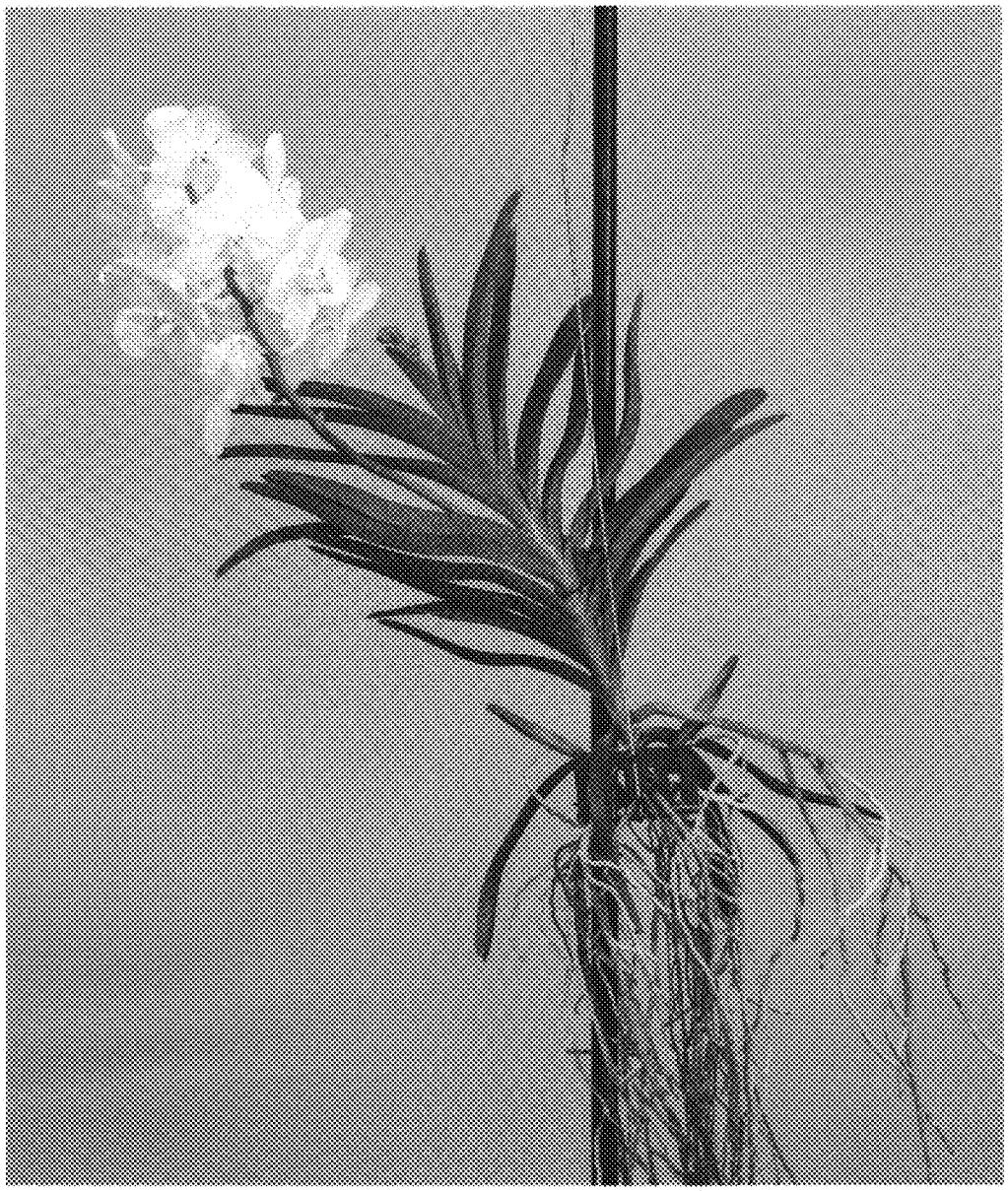
FIG. 1 illustrates, as nearly true as it is reasonably possible to make the same in color photographs of this type, an exemplary plant of 'SPCDW1516' grown in a commercial greenhouse in Honselersdijk, the Netherlands. This plant is approximately 6 years old from the time of mericloning, shown planted in an 8 by 8 cm container.
Figure 2:
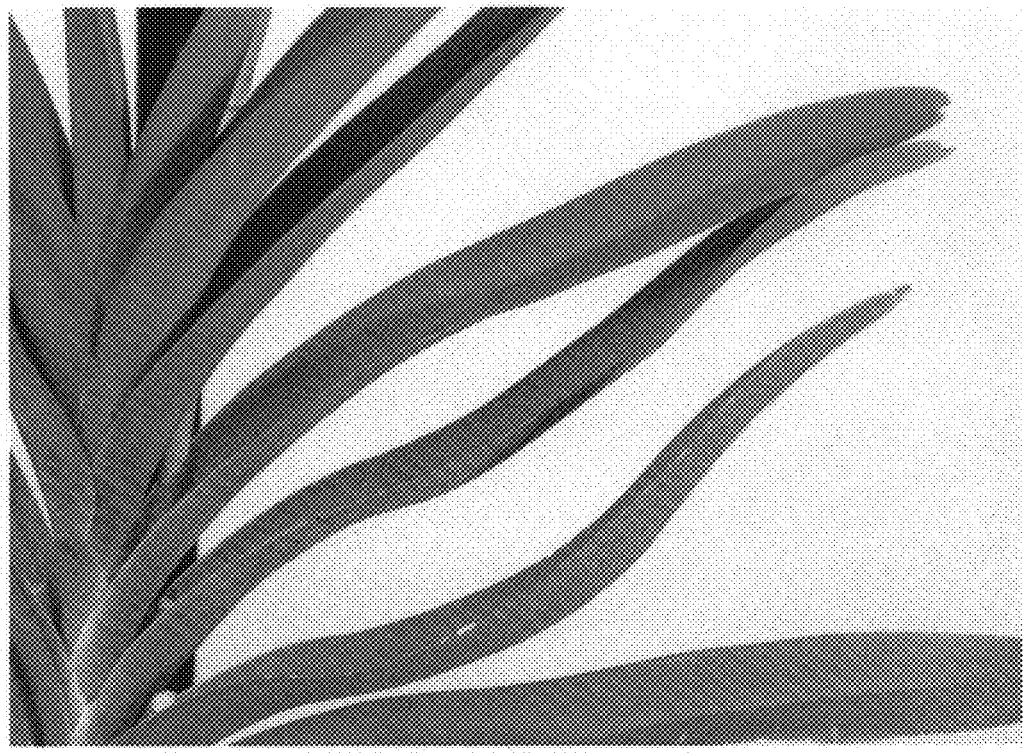
FIG. 2 illustrates, as nearly true as it is reasonably possible to make the same in color photographs of this type, the typical foliage of 'SPCDW1516'.
Figure 3:
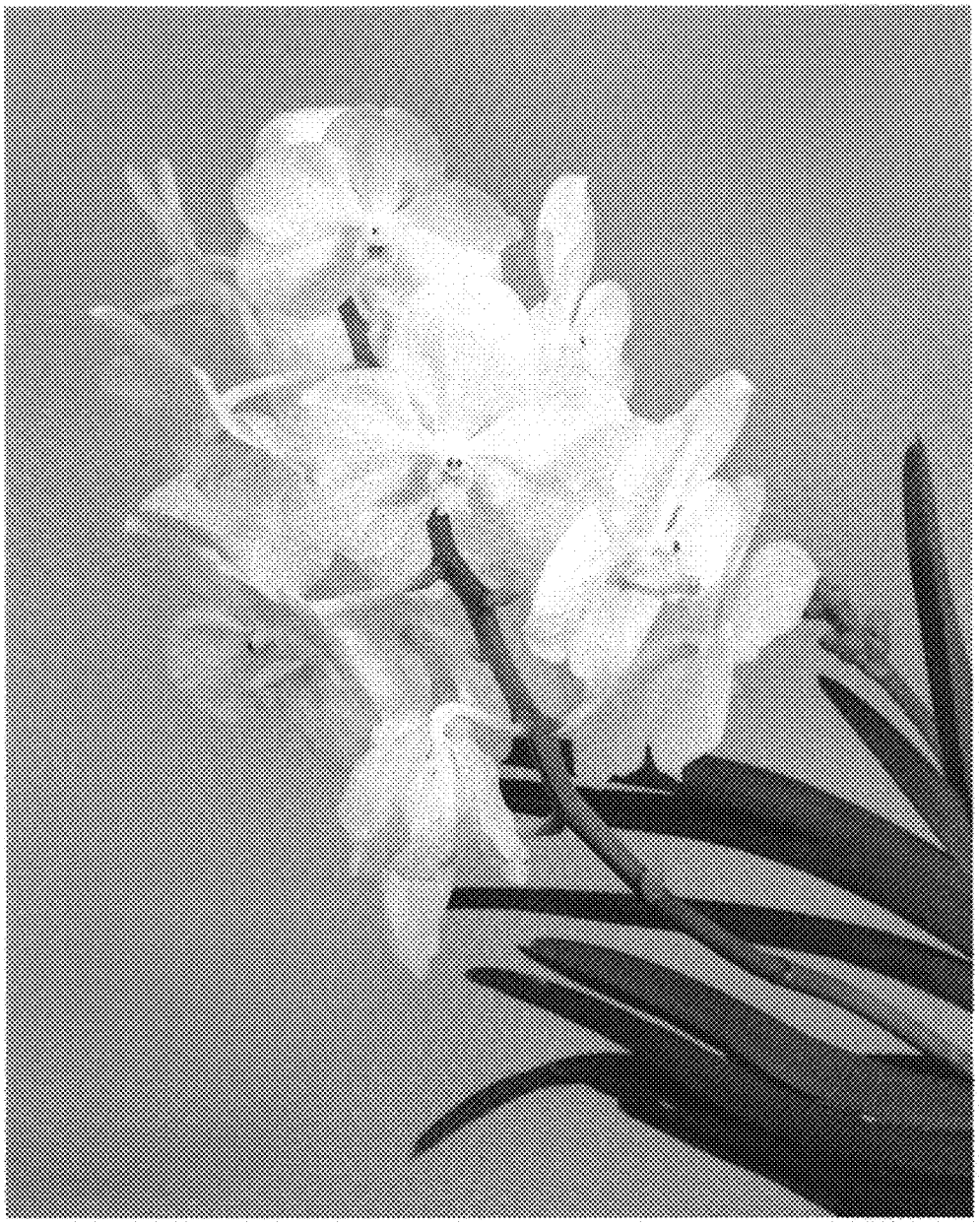
FIG. 3 illustrates, as nearly true as it is reasonably possible to make the same in color photographs of this type, the typical inflorescence of 'SPCDW1516'.
Figure 4:
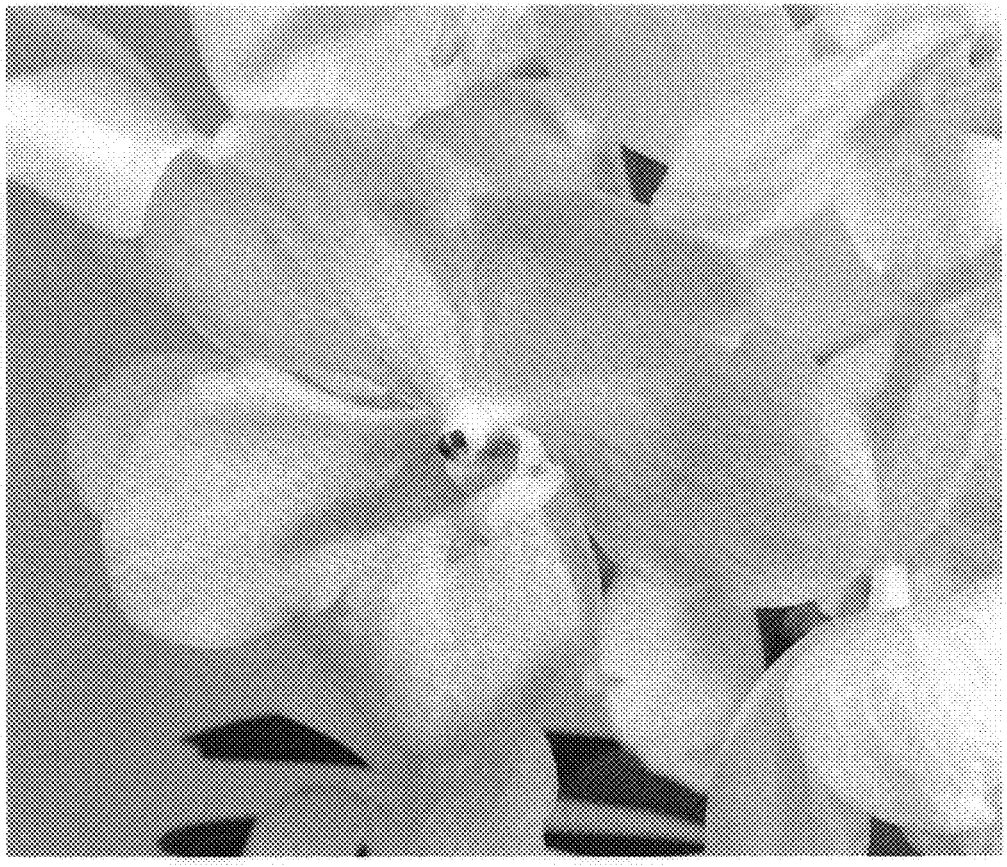
FIG. 4 illustrates, as nearly true as it is reasonably possible to make the same in color photographs of this type, the typical flower of 'SPCDW1516'.

The following observations and measurements made in October of 2016 describe averages from a sample set of six specimens of six year-old 'SPCDW1516' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1516' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'SPCDW1516' and comparisons with other varieties of *Vanda* are provided below.

Plant description:

- *Growth habit.*—Perennial; monopodial, upright. Single monopodial leafy stem, with flowers carried slightly above the leaf plane; inflorescences growing from the leaf axils.
- *Average height from base (plant grown in hanging basket, so no soil line present) to foliar plane.*—42.4 cm.
- *Average height from base (plant grown in hanging basket, so no soil line present) to top of floral plane.*—54.0 cm.
- *Plant spread.*—Average of 37.3 cm.
- *Appropriate container size.*—8 cm by 8 cm rectangular hanging basket.
- *Growth rate.*—Moderate.
- *Plant vigor.*—Moderate.
- *Propagation type.*—Meristematic tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Plants have not been observed to be susceptible or resistant to pathogens and pests common to *Vanda.*
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Moderately to densely rooting; with aerial roots only.
- *Dimensions, mature roots.*—75.0 cm long with a diameter of 0.5 cm, on average.
- *Texture.*—Very fleshy; non-fibrous.
- *Color.*—Greyed-green, in between RHS 192B and 192C; root apex is yellow-green, RHS 146B.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—27.0 cm.
- *Diameter.*—0.9 cm.
- *Internode length.*—0.8 cm.
- *Luster.*—Matte.
- *Aspect.*—Near vertical.
- *Strength.*—Very strong.
- *Color, juvenile.*—Yellow-green, in between RHS 145B and 145C.
- *Color, mature.*—Yellow-green, in between RHS 145B and 145C.
- *Color at internodes.*—Yellow-green, in between RHS 145B and 145C.
- *Pubescence.*—Glabrous.

Foliage:

- *Arrangement.*—Distichous.
- *Dimensions.*—22.0 cm long, excluding the sheath, and 2.5 cm wide.
- *Shape of blade.*—Ligulate; moderately to strongly carinate.
- *Aspect.*—Slightly curved.
- *Apex.*—Unequal praemorse.
- *Base.*—Sheathing.
- *Sheath dimensions.*—3.2 cm long and 1.1 cm wide, on average.
- *Sheath color.*—Yellow-green, in between RHS 145A and 145B.
- *Margin.*—Entire.
- *Pubescence, texture and luster of adaxial surface.*—Glabrous, smooth, and very slightly glossy.
- *Pubescence, texture and luster of abaxial surface.*—Glabrous, smooth, and matte.
- *Color.*—Variegation — Absent. Juvenile foliage, adaxial surface — Green, a mixture of RHS 137B and RHS 143A. Juvenile foliage, abaxial surface — Green, nearest to RHS 143A. Mature foliage, adaxial surface — Green, nearest to RHS 137B. Mature foliage, abaxial surface — Yellow-green, nearest to RHS 146B.
- *Venation.*—Parallel.
- *Venation color, adaxial surface.*—Green, nearest to RHS 137B.
- *Venation color, abaxial surface.*—Yellow-green, in between RHS N144C and N144D.
- *Petiole.*—No petioles present; leaves sessile.

Inflorescence:

*Inflorescence arrangement*.—Axially placed raceme.

*Natural flowering season*.—Autumn into winter.

*Time to flower*.—Approximately 10 months.

*Quantity of inflorescence per plant*.—One.

*Flowers per inflorescence*.—Average of 12.

*Flowers per plant*.—20 open flowers and 4 flower buds.

*Inflorescence height*.—Approximately 22.0 cm (measured from base of lowest flower to top of upper flower).

*Inflorescence diameter*.—Approximately 16.2 cm.

*Peduncle*.—Dimensions — Approximately 34.5 cm long and 0.7 cm wide. Aspect — Generally at a 35 degree angle to lateral branch axis. Strength — Moderately strong. Texture and luster — Glabrous and moderately glossy. Color — Green, nearest to RHS 143C.

Bud:

*Length*.—Average of 2.1 cm.

*Diameter*.—Average horizontal diameter is 1.8 cm; the vertical diameter is 1.8 cm.

*Shape*.—Cubic, with a deltoid apex which is pointed downward.

*Pubescence, texture and luster*.—Glabrous, smooth and very slightly glossy.

*Color*.—A mixture of yellow-green, nearest to RHS 150D, and white, RHS 155A; apex is suffused with yellow-green, RHS 154C.

Flower:

*Flower type*.—Zygomorphic (orchidaceous), typical shape for the genus *Vanda*.

*Flowering habit*.—Moderate.

*Shape*.—Zygomorphic, single; consisting of three sepals and three petals, one of which is transformed into a labellum; the two lateral petals slightly overlapping the sepals; sepals do not overlap one another.

*Aspect*.—Flowers are outward-facing to slightly nodding.

*Vertical height*.—Approximately 8.7 cm.

*Diameter*.—Approximately 8.6 cm.

*Depth*.—Approximately 2.7 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 4.4 cm. Width — Approximately 3.4 cm. Shape — Broad ovate. Apex — Undeeply retuse to obtuse. Base — Cuneate. Margin — Entire; slightly undulated. Pubescence, texture and luster of upper surface — Glabrous, velvety and matte. Pubescence, texture and luster of lower surface — Glabrous, velvety and matte. Color when opening, upper surface — White, nearest to RHS NN155A; apex is suffused with green-white, nearest to RHS 157C. Color when opening, lower surface — White, nearest to RHS NN155A; apex is suffused with green-white, nearest to RHS 157B. Color when fully opened, upper surface — White, nearest to NN155D; lower half is white, RHS NN155C. Color when fully opened, lower surface — White, nearest to NN155D; lower half is white, RHS NN155C. Fading, upper surface — Not fading. Fading, lower surface — Not fading. Venation — Densely reticulate. Venation color, fully opened, upper surface — White, nearest to NN155D; lower half is white, RHS NN155C. Venation color, fully opened, lower surface — White, nearest to NN155D; lower half is white, RHS NN155C.

*Labellum*.—Shape — Three-lobed; the shape of the lateral lobes is triangular, and the aspect is involute; the shape of the central lobe is narrow triangular, and the aspect is revolute. Length — Central lobe — Approximately 1.8 cm. Lateral lobes — Approximately 0.8 cm. Width — Central lobe — Approximately 1.0 cm. Lateral lobes — Approximately 0.55 cm. Apex — Central lobe — Strongly emarginate. Lateral lobes — Emarginate. Base — Central lobe — Cuneate. Lateral lobes — Cuneate. Margin — Central lobe — Entire; not undulate. Lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Yellow-green, nearest to RHS 150C, and fading to yellow at the base, in between RHS 12A and 12B. Lateral lobes — Yellow-green, nearest to RHS 150D; dotted purple and yellow-orange at the base, a mixture of to RHS 75B and RHS 17B. Color when opening, lower surface — Central lobe — Yellow-green, nearest to RHS 145C, and fading lighter towards the base, nearest to RHS 150D. Lateral lobes — A mixture of yellow-green, RHS 150D, and white, RHS 155A. Color when fully opened, upper surface — Central lobe — Yellow-green, nearest to RHS 150D, and fading to white towards the base, nearest to RHS 155A. Lateral lobes — White, nearest to RHS NN155B, and suffused with yellow-green at the apex, nearest to RHS 150D; dotted purple and yellow at the base, a mixture of RHS N75D and RHS 12C. Color when fully opened, lower surface — Central lobe — Yellow-green, nearest to a mixture of RHS 150D and 151D and fading white towards the base, nearest to RHS NN155B. Lateral lobes — White, RHS NN155C. Fading, upper surface — Not fading. Fading, lower surface — Not fading. Venation — Densely reticulate. Venation color, fully opened, upper surface — Central lobe — Yellow-green, nearest to RHS 150D, and fading white towards the base, nearest to RHS 155A. Lateral lobes — White, nearest to RHS NN155B, and suffused with yellow-green at the apex, nearest to RHS 150D; dotted purple and yellow at the base, a mixture of RHS N75D and RHS 12C. Venation color, fully opened, lower surface — Central lobe — Yellow-green, nearest to a mixture of RHS 150D and 151D and fading white towards the base, nearest to RHS NN155B. Lateral lobes — White, RHS NN155C.

*Callosities*.—Dimensions — 1.2 cm long and 0.6 cm wide, on average. Color — White, nearest to RHS NN155B.

*Spurs*.—Quantity — Average of 1. Length — Approximately 0.9 cm. Diameter — Approximately 0.2 cm. Vertical height — Approximately 0.5 cm, at the base. Shape — Short triangular. Apex — Bluntly acute. Base — Broad cuneate. Pubescence, texture and luster — Glabrous, smooth, and slightly glossy. Color — White, a mixture of RHS N155B and N155C.

*Sepals*.—Quantity — Average of 3 unfused sepals. Arrangement — One dorsal sepal and two lateral sepals. Length — Dorsal sepal — Approximately 4.4 cm. Lateral sepals — Approximately 4.8 cm. Width — Dorsal sepal — Approximately 3.8 cm. Lateral sepals — Approximately 4.4 cm. Shape — Dorsal sepal — Broad ovate to near orbicular. Lateral sepals — Broad ovate to near orbicular. Apex — Dorsal sepal — Obtuse. Lateral sepals — Obtuse. Base — Dorsal sepal — Cuneate. Lateral sepals — Cuneate. Margin — Dorsal sepal — Entire; slightly undulated. Lateral sepals — Entire; slightly undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — White, nearest to RHS 155A, and lightly suffused with yellow-green, especially towards the apex, in between RHS 145C and RHS 145D. Lateral sepals — White, nearest to RHS 155A, and lightly suffused with yellow-green, especially towards the apex, in between RHS 145C and RHS 145D. Color when opening, lower surface — Dorsal sepal — White, nearest to RHS 155A, and a lightly suffused with yellow-green, especially towards the apex, in between RHS 145C and RHS 145D. Lateral sepals — White, nearest to RHS 155A, and lightly suffused with yellow-green, especially towards the apex, in between RHS 145C and RHS 145D. Color when fully opened, upper surface — Dorsal sepal — White, nearest to RHS NN155C. Lateral sepals — White, nearest to RHS NN155B, and lightly suffused with yellow-green, nearest to RHS 150D. Color when fully opened, lower surface — Dorsal sepal — White, nearest to RHS NN155C. Lateral sepals — White, nearest to RHS NN155B, and lightly suffused with slightly darker, nearest to RHS 155A. Fading, upper surface — Not fading. Fading, lower surface — Not fading. Venation — Densely reticulate. Venation color, fully opened, upper surface — Dorsal sepal — White, nearest to RHS NN155C. Lateral sepals — White, nearest to RHS NN155B, and suffused with yellow-green, nearest to RHS 150D. Venation color, fully opened, lower surface — Dorsal sepal — White, nearest to RHS NN155C. Lateral sepals — A mixture of white, nearest to RHS NN155B, and slightly darker white, nearest to RHS 155A.

*Pedicels*.—Length — Approximately 4.7 cm. Diameter — Approximately 0.35 cm. Angle — Approximately 90 degree angle to peduncle axis. Strength — Moderate. Texture — Glabrous, axially angled with 5 "ribs", axially twisted (due to resupination). Luster — Glossy. Color — White, nearest to RHS NN155B, and suffused with yellow-green, nearest to RHS 145B, towards the proximal end.

*Bract*.—Quantity — One bract present at the base of each pedicel. Shape — Broad ovate; folded around the base of each pedicel. Dimensions — Average of 1.0 cm long and 1.1 cm wide. Apex — Broad acute. Base — Broad cuneate. Margins — Entire. Color, both surfaces — Yellow-green, nearest to RHS N144B.

Reproductive organs:

*Column*.—Length — Approximately 0.6 cm. Diameter — Approximately 0.5 cm. Color — White; a mixture of RHS NN155A and NN155B.

*Ovary*.—Position — Inferior. Diameter — Approximately 0.2 cm. Color — Yellow-green, RHS 150C.

*Pollinia color*.—Yellow-orange, RHS 14A.

Seed and fruit: No fruit and seed production has been detected to date.

Comparison With the Parent Plant

Plants of the new cultivar 'SPCDW1516' differ from the *Vanda* parent plant 'SPCDW1001' (Community Plant Variety Rights grant number 29778) by the characteristics described in Table 1.

TABLE 1

| Characteristic | 'SPCDW1516' | 'SPCDW1001' |
|---|---|---|
| General coloration of petals when fully opened. | Relatively more white than 'SPCDW1001'. | Relatively less white than 'SPCDW1516'. |
| General coloration of sepals when opening and when fully opened. | Relatively more white than 'SPCDW1001' with less pronounced yellow-green suffusion; lateral sepals are nearly white with very little yellow-green suffusion. | Relatively less white than 'SPCDW1516' with more pronounced yellow-green suffusion. |
| General coloration of the central lobe of the labellum when fully opened. | Lighter yellow-green compared to 'SPCDW1001'. | Darker yellow-green compared to 'SPCDW1516'. |
| Width of the central lobe of the labellum. | Narrower than the central lobe of 'SPCDW1001'. | Wider than the central lobe of 'SPCDW1516'. |

Comparison With the Most Similar *Vanda* Cultivar Known to the Inventor

Plants of the new cultivar 'SPCDW1516' are most similar to the cultivar, *Vanda* 'SPCDW0902' (U.S. Plant Pat. No. 23,343). A comparison of 'SPCDW1516' with *Vanda* 'SPCDW0902' is described in Table 2.

TABLE 2

| Characteristic | 'SPCDW1516' | 'SPCDW0902' |
|---|---|---|
| Flower size. | Larger than 'SPCDW0902'. | Smaller than 'SPCDW1516'. |
| General coloration of petals when opening. | Relatively more white than 'SPCDW0902' with less pronounced green-white suffusion. | Relatively less white than 'SPCDW1516' with more pronounced green-whitesuffusion. |
| General coloration of petals when fully opened. | Relatively more white than 'SPCDW0902'. | Relatively less white than 'SPCDW1516'. |
| General coloration of sepals when opening | Relatively more white than 'SPCDW0902' | Relatively less white than 'SPCDW1516' |

TABLE 2-continued

| Characteristic | 'SPCDW1516' | 'SPCDW0902' |
|---|---|---|
| and when fully opened. | with less pronounced yellow-green suffusion; lateral sepals are nearly white with very little yellow-green suffusion. | with more pronounced yellow-green suffusion. |
| Overlapping of petals and sepals. | Less overlapped when compared to 'SPCDW0902'. | More overlapped when compared to 'SPCDW1516'. |
| Apex of dorsal sepal. | Less rounded than 'SPCDW0902'. | More rounded than 'SPCDW1516'. |
| Apex of petals. | Less rounded than 'SPCDW0902'. | More rounded than 'SPCDW1516'. |
| General coloration of the central lobe of the labellum when fully opened. | Lighter yellow-green compared to 'SPCDW0902'. | Darker yellow-green compared to 'SPCDW1516'. |
| General coloration of lateral lobes of the labellum when fully opened. | Nearly white with less pronounced light yellow-green suffusion, and dotted purple and yellow at the base. | Relatively less white with more pronounced yellow-green suffusion. |

That which is claimed is:

1. A new and distinct variety of *Vanda* plant named 'SPCDW1516', substantially as described and illustrated herein.

* * * * *